(12) United States Patent
Miura et al.

(10) Patent No.: US 8,287,839 B2
(45) Date of Patent: Oct. 16, 2012

(54) CARBORANYLPORPHYRINS AND USES THEREOF

(75) Inventors: Michiko Miura, Hampton Bays, NY (US); Mark W. Renner, Hampton Bays, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 1310 days.

(21) Appl. No.: 11/633,139

(22) Filed: Dec. 4, 2006

(65) Prior Publication Data

US 2008/0131376 A1    Jun. 5, 2008

(51) Int. Cl.
| A61K 51/00 | (2006.01) |
| A61M 36/14 | (2006.01) |
| C07B 47/00 | (2006.01) |
| C07D 487/22 | (2006.01) |
| C07D 345/00 | (2006.01) |
| C07D 517/00 | (2006.01) |

(52) U.S. Cl. .......... 424/1.11; 424/1.61; 540/1; 540/145
(58) Field of Classification Search .................. 540/145; 424/1.61
See application file for complete search history.

(56) References Cited

U.S. PATENT DOCUMENTS

| 4,783,529 A | 11/1988 | Lavallee et al. |
| 4,824,659 A | 4/1989 | Hawthorne |
| 4,892,941 A | 1/1990 | Dolphin et al. |
| 4,959,356 A | 9/1990 | Miura et al. |
| 4,977,268 A | 12/1990 | McPhail et al. |
| 5,149,801 A | 9/1992 | Kahl et al. |
| 5,162,231 A | 11/1992 | Cole et al. |
| 5,268,371 A | 12/1993 | Mauclaire et al. |
| 5,312,896 A | 5/1994 | Bhardwaj et al. |
| 5,466,679 A | 11/1995 | Soloway et al. |
| 5,563,132 A | 10/1996 | Bodaness |
| 5,599,796 A | 2/1997 | Schinazi et al. |
| 5,654,423 A | 8/1997 | Kahl et al. |
| 5,672,334 A | 9/1997 | Ranney |
| 5,674,467 A | 10/1997 | Maier et al. |
| 5,679,322 A | 10/1997 | Wilbur |
| 5,707,604 A | 1/1998 | Ranney |
| 5,776,925 A | 7/1998 | Young et al. |
| 5,877,165 A | 3/1999 | Miura et al. |
| 5,955,586 A | 9/1999 | Sessler et al. |
| 6,010,805 A | 1/2000 | Scanlon, Jr. et al. |
| 6,066,628 A | 5/2000 | Stojiljkovic et al. |
| 6,375,930 B2 | 4/2002 | Young et al. |
| 6,566,517 B2 | 5/2003 | Miura et al. |
| 6,759,403 B2 | 7/2004 | Miura et al. |
| 6,765,092 B2 | 7/2004 | Lindsey et al. |
| 6,849,607 B2 | 2/2005 | Pandey et al. |
| 6,906,050 B2 | 6/2005 | Robinson |
| 6,951,640 B2 | 10/2005 | Miura et al. |
| 6,958,389 B2 | 10/2005 | Yano et al. |
| 6,989,443 B2 | 1/2006 | Wu et al. |
| 6,995,260 B2 | 2/2006 | Wu et al. |
| 7,067,653 B2 | 6/2006 | Vicente et al. |
| 7,087,214 B2 | 8/2006 | Bart et al. |
| 2002/0025298 A1 | 2/2002 | Blumenkranz |
| 2004/0019095 A1 | 1/2004 | Xiao et al. |
| 2004/0022734 A1 | 2/2004 | Bourre et al. |
| 2004/0106592 A1 | 6/2004 | Vicente |
| 2004/0215012 A1 | 10/2004 | Kool et al. |
| 2004/0259810 A1 | 12/2004 | Grierson et al. |
| 2005/0260128 A1 | 11/2005 | Wu et al. |
| 2007/0027312 A1* | 2/2007 | Lindsey et al. ............... 540/145 |
| 2007/0093463 A1* | 4/2007 | Miura et al. .................. 514/185 |

FOREIGN PATENT DOCUMENTS

| WO | WO 01/85736 A1 | 11/2001 |
| WO | WO 2004/030661 | 4/2004 |

OTHER PUBLICATIONS

Arnold et al. (Aust. J. Chem. 1997, 50, 495-503).*
Humphrey et al. (J. Phys. Chem. B 2005, 108, 12016-12023).*
Mody (J. Porphyrins and Phthalocyanines 2000, 4, 362-367).*
Wielopolski, L. (Analysis of Accelerator Based Neutron Spectra for BNCT Using Proton Recoil Spectroscopy, Rpt. BNL-66068, 1998).*
Wu et al., "Total syntheses of three copper (II) tetracarboranylphenylporphyrins containing 40 or 80 boron atoms and their biological properties in EMT-6 tumor-bearing mice," *Biorganic & Medicinal Chemistry*, 14: 5083-5092 (2006).
Morris et al., "Porphyrin-mediated boron neutron capture therapy: evaluation of the reactions of skin and central nervous system," *Int. J. Radiat. Biol.*, 79(3): 149-158 (2003).
Vicente, et al., "Synthesis, dark toxicity and induction of in vitro DNA photodamage by a tetra (4-*nido*-carboranylphenyl)prophyrin," *J. Photochem. Photobiol. B. Biology*, 68(2-3): 123-132 (2002).
Maderna et al., "Synthesis of a porphyrin-labelled carboranyl phosphate diester: a potential new drug for boron neutron capture therapy of cancer," *Chem. Commun.*, 16: 1784-1785 (2002).
Miura et al., "Boron Neutron Capture of a Murine Mammary Carcinoma using a Lipophilic Carboranyltetraphenylporphyrin," *Radiat. Res.*, 155(4): 603-610 (2001).
Miura et al., "Evaluation of carborane-containing porphyrins as tumor targeting agents for boron neutron capture therapy," *Br. J. Radiol.*, 71(847): 773-781 (1998).
Miura et al., "Synthesis of a Nickel Tetracarboranylphenylporphyrin for Boron Neutro-Capture. Therapy: Biodistribution and Toxicity in Tumor-Bearing Mice," *Int. J Cancer*, 68(1): 114-119 (1996).
Kahl et al., "A Carboranyl Porphyrin for Boron Neutron Capture Therapy of Brain Tumors," *Basic Life Sci.*, 50: 193-203 (1989).
Miura et al., "Biodistribution of copper carboranyltetraphenylporphyrins in rodents bearing an isogeneic or human neoplasm," *J. NeuroOncol*, 5: 111-117 (2001).

(Continued)

*Primary Examiner* — Michael G Hartley
*Assistant Examiner* — Melissa Perreira
(74) *Attorney, Agent, or Firm* — Dorene M. Price

(57) ABSTRACT

The present invention is directed to low toxicity boronated compounds and methods for their use in the treatment, visualization, and diagnosis of tumors. More specifically, the present invention is directed to low toxicity carborane-containing porphyrin compounds with halide, amine, or nitro groups and methods for their use particularly in boron neutron capture therapy (BNCT), X-ray radiation therapy (XRT), and photodynamic therapy (PDT) for the treatment of tumors of the brain, head and neck, and surrounding tissue. The invention is also directed to using these carborane-containing porphyrin compounds in methods of tumor imaging and/or diagnosis such as MRI, SPECT, or PET.

12 Claims, No Drawings

OTHER PUBLICATIONS

Berlin et al., "Are Porphyrin Mixtures Favorable Photodynamic Anticancer Drugs? A Model Study with Combinatorial Libraries of Tetraphenylporphyrins," *Combinatorial Chemistry*, 61(2): 107-118 (1998).

Miller et al., "In Vivo Animal Studies with Gadolinium (III) Texaphyrin As a Radiation Enhancer," *Int. J. Radiat. Oncol. Biol. Phys.*, 45(4): 981-989 (1999).

Bhyrappa et al., "Octabromotetraphenylporphyrin and Its Metal Derivatives: Electronic Structure and Electrochemical Properties," *Inorg. Chem.*, 30: 239-245 (1991).

Birnbaum et al., "$^{19}$F NMR Spectra and Structures of Halogenated Porphyrins," *Inorg. Chem.*, 34(14): 3625-3632 (1995).

Fairchild et al., "Current Status of $^{10}$B-Neutron Capture Therapy: Enhancement of Tumor Dose Via Beam Filtration and Dose Rate, and the Effects of These Parameters on Minimum Boron Content: a Theoretical Evaluation," *Int. J Radiat. Oncol. Biol. Phys.*, 11(4): 831-840 (1985).

Woller et al., "2, 3, 7, 8, 12, 13, 17, 18-Octafluoro-5, 10, 15, 20-tetraarylporphyrins and Their Zinc Complexes: First Spectroscopic, Electrochemical, and Structural Characterization of a Perfluorinated Tetraarylmetalloporphyrin," *J. Org. Chem.*, 62(6): 1588-1593 (1997).

Woller et al., "A Straightforward Synthesis of 3,4-Difluoropyrrole," *J. Org. Chem:*, 63(16): 5706-5707 (1998).

Ozette et al., "New Metalloporphyrins with Extremely Altered Redox Properties: Synthesis, Structure, and Facile Reduction to Air-Stable π-Anion Radicals of Zinc and Nickel β-Heptanitroporphyrins," *J. Am. Chem. Soc.*, 119(27): 6442-6443 (1997).

Chanana et al., "Boron Neutron Capture Therapy for Glioblastoma Multiforme: Interim Results from the Phase I/II Dose-Escalation Studies," *Neurosurgery*, 44(6): 1182-1193 (1999).

Vicente et al., "Syntheses of carbon—carbon linked carboranylated porphyrins for boron neutron capture therapy of cancer." *Tetrahedron Letters*, 41: 7623-7627 (2000).

Evstigneeva, "Synthesis of Carboranylporphyrins and the Perspectives of Their Use for Boron Neutron Capture Therapy," *Molecules*, 5: 1479-80 (2001).

Zakharkin et al., "Synthesis of carboranyl derivatives of deuteroporphyrin IX," *Russian Chemical Bulletin*, 48(12): 2312-14 (1999).

Harth et al., "The Effect of Macromolecular Architecture in Nanomaterials: A comparison of Site Isolation in Polyphyrin Core Dedrimers and Their Isomeric Linear Analogues," *J. Am. Chem Soc.* 124: 3926-3938 (2002).

Frixa et al., "Synthesis of meso-substituted porphyrins carrying carboranes and oligo(ethylene glycol) units for potential applications in boron neutron capture therapy," *Org. Biomol. Chem.*, 1: 306-317 (2003).

Foye et al., "Principles of Medicinal Chemistry," Fourth Edition, *Williams and Wilkins*, 902-907 (1995).

Vitale et al., "Boron-Containing Bioactive Molecules: An Approach to Boron Neutron Capture Therapy," *Molecular Medicinal Chemistry*, 8: 1-49 (2005).

Carr et al., "Carborane Complexes of Nickel and Platinum: Synthesis and Protonation Reactions of Anionic Allyl (carborane) Species," *Inorg. Chem.*, 33:.1666-1673 (1994).

Plumb et al., "Tricarbon Carborane Chemistry. 1. Synthesis and Structural Characterizations of Monocage Iron, Manganese, and Nickel Metallatricarbaborane Complexes," *Organometallics*, 11: 1665-1671 (1992).

Teixidor et al., "Macrocycles Incorporating Sulfur and *nido*-Carborane Cages: Reactivity toward Nickel (II) and Palladium (II)," *Inorg. Chem.* 30: 3053-3058.

Capala et al., "Accumulation of Boron in Malignant and Normal Cells Incubated In Vitro with Boronophenylalanine, Mercaptoborane or Boric Acid," *Radiation Research Society*, 146: 554-560 (1996).

Coderre et al., "Boron neutron capture therapy for glioblastoma multiforme using *p*-boronophenylalanine and epithermal neutrons: Trial design and early clinical results," *Journal of Neuro-Oncology*, 33: 141-152 (1997).

Coderre et al., "Neutron Capture Therapy of the 9L Rat Gliosarcoma Using the *P*-Boronophenylalanine-Fructose Complex," *Int. J. Radiation Oncology Biol. Phys*. 30:(3) 643-652 (1994).

Fairchild et al., "Microanalytical techniques for boron analysis using the $^{10}$B$(n,a)^7$Li reaction $^{a)b)}$," *Med. Phys*. 13:(1)50-56, (1986).

Coderre et al., "Selective Delivery of Boron by the Melanin Precursor Analogue *p*-Boronophenylalanine to Tumors Other Than Melanoma," *Cancer Research*, 50: 138-141 (1990).

Miura et al., "Biodistribution and Toxicity of 2,4-Divinyl-Nido-*o*-Carboranyldeuteroporphyrin IX in Mice," *Biochemical Pharmacology*, 43:3, 467-476, (1992).

Miura et al., "Synthesis of a Nickel Tetracarboranylphenylporphyrin for Boron Neutro-Capture Therapy: Biodistribution and Toxicity in Tumor-Bearing Mice," *Int. J. Cancer*, 68(1): 114-119 (1996).

Fairchild et al., "Current Status of $^{10}$B-Neutron Capture Therapy: Enhancement of Tumor Dose Via Beam Filtration and Dose Rate, and the Effects of These Parameters on Minimum Boron Content: a Theoretical Evaluation," *Int. J. Radiat. Oncol. Biol. Phys.*, 11(4): 831-840 (1985).

Woller et al., "A Straightforward Synthesis of 3,4-Difluoropyrrole," *J. Org. Chem.*, 63(16): 5706-5707 (1998).

Sol, et al., "Synthesis, Spectroscopy, and Photocytotoxicity of Glycosylated Amino Acid Porphyrin Derivatives as Promising Molecules for Cancer Phototherapy," *J. Org. Chem.*, 64: 4431-4444 (1999).

Oulmi, et al., "Glycoconjugated Porphyrins. 3. Synthesis of Flat Amphiphilic Mixed *meso*-(Glycosylated aryl)arylporphyrins and Mixed *meso*-(Glycosylated aryl)alkylporphyrins Bearing Some Mono- and Disaccharide Groups," *J. Org. Chem.*, 60: 1554-1564 (1995).

Sylvain, et al., "Synthesis and Biological Evaluation of Thioglycosylated Porphyrins for an Application in Photodynamic Therapy," *Bioorg Med Chem.*, 10:57-69 (2002).

Frochot, et al., "New Glycosylated Porphyrins for PDT Applications," *Oftalmologia 1*, 56(1):62-6 (2003).

Schell, et al., "Synthesis and Investigation of Glycosylated Mono- and Diarylporphyrins for Photodynamic Therapy," *Bioorg Med Chem.*, 7:1857-1865 (1999).

Kaldapa, et al., "Synthesis of New Glycosylated Neutral and Cationic Porphyrin Dimers," *Tetrahedron Letters*, 4:331-335 (2000).

Bourhim, et al., "Synthesis of New Glycosylated Porphyrin Derivatives with a Hydrocarbon Spacer Arm," *SYNLETT*, 8:563-564 (1993).

Maillard, et al., "Glycoconjugated Porphyrins. 2. Synthesis of Sterically Constrained Polyglycosylated Compounds Derived from Tetraphenylporphyrins," *J. Org. Chem.*, 58:2274-2780 (1993).

Gong, et al., "Amperometric Metronidazole Sensor Based on the Supermolecular Recognition by Metalloporphyrin Incorporated in Carbon Paste Electrode," *Sensors*, 3:91-100 (2003).

Carr et al., "Carborane Complexes of Nickel and Platinum: Synthesis and Protonation Reactions of Anionic Allyl (carborane) Species," *Inorg. Chem.*, 33: 1666-1673 (1994).

Teixidor et al., "Macrocycles Incorporating Sulfur and *nido*-Carborane Cages: Reactivity toward Nickel (II) and Palladium (II)," *Inorg. Chem.* 30: 3053-3058 (1991).

Coderre et al., "Neutron Capture Therapy of the 9L Rat Gliosarcoma Using the *P*-Boronophenylalanine-Fructose Complex," *Int. J. Radiation Oncology Biol. Phys.* 30, (3) 643-652 (1994).

Fairchild et al., "Microanalytical techniques for boron analysis using the $^{10}$B$(n,a)^7$Li reaction $^{a)b)}$," *Med. Phys.* 13: (1) 50-56, (1986).

Miura et al., "Biodistribution and Toxicity of 2,4-Divinyl-Nido-*o*-Carboranyldeuteroporphyrin IX in Mice," *Biochemical Pharmacology*, 43: 3, 467-476, (1992).

\* cited by examiner

text follows …

CARBORANYLPORPHYRINS AND USES THEREOF

The invention was made with government support under Contract No. DE-AC02-98CH10886 awarded by the U.S. Department of Energy. The Government has certain rights in the invention.

BACKGROUND OF THE INVENTION

The efficacy of radiation and chemical methods in the treatment of cancers has been limited by a lack of selective targeting of tumor cells by the therapeutic agent. In an effort to spare normal tissue, current tumor treatment methods have therefore restricted radiation and/or chemical treatment doses to levels that are well below optimal or clinically adequate. Thus, designing compounds that are capable, either alone or as part of a therapeutic method, of selectively targeting and destroying tumor cells, is a field of intense study.

Because of the known affinity of porphyrins to neoplastic tissues, there has been intense interest in using porphyrins as delivery agents in the treatment of neoplasms in brain, head and neck, and related tumors. Porphyrins in general belong to a class of colored, aromatic tetrapyrrole compounds, some of which are found naturally in plants and animals, e.g., chlorophyll and heme, respectively.

Porphyrins and other tetrapyrroles with relatively long triplet lifetimes have already been used to treat malignant tumors using photodynamic therapy (PDT). In PDT, the patient is first injected with a photosensitizing drug, typically a porphyrin. The tumor cells, now photosensitized, are susceptible to destruction when exposed to an intense beam of laser red light. The biochemical mechanism of cell damage in PDT is believed to be mediated largely by singlet oxygen, which is produced by transfer of energy from the light-excited porphyrin molecule to an oxygen molecule. However, PDT has been limited predominantly by the limited penetration of red light, which is only a few millimeters in depth.

X-ray radiation therapy (XRT) is the most commonly used radiation treatment for numerous forms of cancer. In conventional XRT, a patient is irradiated by fractionated X-ray radiotherapy without a radiosensitizing drug. However, if a radiosensitizing drug is injected prior to irradiation, the tumor cells, now radiosensitized, are more susceptible than surrounding tissues to destruction when exposed to X-ray radiation. X-rays are classified as low linear-energy-transfer (LET) radiation because of the rate at which the type of radiation deposits energy as it passes through tissue. The compounds currently used in clinical XRT have not yet demonstrated a high rate of tumor control in the treatment of head and neck and other deadly cancers.

A promising new form of high LET radiation cancer therapy is boron neutron-capture therapy (BNCT). BNCT is a bimodal cancer treatment based on the selective accumulation of a stable nuclide of boron known as boron-10, or $^{10}$B, in the tumor, followed by irradiation of the tumor with thermalized neutrons. The thermalized neutrons impinge on the boron-10, causing nuclear fission (decay reaction). The nuclear fission reaction causes the highly localized release of vast amounts of energy in the form of high (LET) radiation, which can kill cells more efficiently (higher relative biological effect) than low LET radiation, such as X-rays.

Boron-10 undergoes the following nuclear reaction when captured by a thermal neutron:

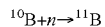

In this nuclear reaction, a boron-10 nucleus captures a neutron forming the metastable nuclide $^{11}$B, which spontaneously and nearly instantaneously disintegrates into a $^{4}$He and $^{7}$Li particle, which together possess an average total kinetic energy of 2.34 MeV. These two ionized particles travel about 9 μm and 5 μm (7±2 μm) in opposite directions in soft tissue, respectively.

The distances traveled by the $^{4}$He and $^{7}$Li particles are comparable to the diameter of many tumor and tumor-associated cells. Therefore, the efficacy of BNCT resides in the production of highly localized, high LET ionizing radiation within the tumor. The targeted tumor thus receives a large dose of radiation while sparing surrounding normal tissue.

In the case of brain tumors, after administration of the boron compound, the patient's head is irradiated in the general area of the brain tumor with an incident beam or field of epithermal (0.5 eV-10 keV) neutrons. The neutrons become progressively thermalized (average energy approximately 0.04 eV) as they penetrate deeper into the head. As the neutrons become thermalized, they are more readily captured by the boron-10 concentrated in the tumor cells and/or tumor supporting tissues, since the capture cross section is inversely proportional to the neutron velocity.

In BNCT, the boron-containing compound must be non-toxic or of low toxicity when administered in therapeutically effective amounts, as well as being capable of selectively accumulating in cancerous tissue. Although BPA has the advantage of low chemical toxicity, it accumulates in critical normal tissues at levels that are less than desirable. In particular, ratios of boron concentration in tumors relative to normal brain and tumors relative to blood are approximately 3:1. Such low specificity limits the maximum dose of BPA to a tumor since the allowable dose to normal tissue is the limiting factor.

Porphyrins are not only useful in the treatment of tumors, but these compounds are also useful in the visualization and diagnosis of tumors. A porphyrin molecule has the advantage of having the ability to chelate metal ions in its interior. Such chelated porphyrins can additionally function as visualization tools for real-time monitoring of porphyrin concentration and/or diagnostic agents. For example, when chelated to paramagnetic metal ions, porphyrins may function as contrast agents in magnetic resonance imaging (MRI), and when chelated to radioactive metal ions, porphyrins may function as imaging agents for single photon emission computed tomography (SPECT) or positron emission tomography (PET).

In addition, by using chelated boron-containing porphyrins in BNCT, boron concentration and distribution in and around the tumor and all tissues within the irradiated treatment volume can be accurately and rapidly determined noninvasively before and during the irradiation. Such diagnostic information allows BNCT treatment to be performed more quickly, accurately, and safely, by lowering exposures of epithermal neutrons in regions of tissues known to contain high levels of boron. Short irradiations would obviate the inconvenience and discomfort to the patient of long and often awkward positioning of the head at a reactor port. However, the anticipated use of accelerator-generated neutrons would likely produce a significantly lower flux and hence effect longer irradiation times, so that compounds that have longer tumor retention times would become critical.

Accordingly, there is a need for new compounds, especially boron-containing porphyrins, with long retention times in tumors, and that selectively target and destroy tumor cells with minimal damage to normal tissue. In addition, there is a need for more effective methods for the treatment of brain, head and neck, and related tumors, and more particularly, more effective XRT and BNCT treatments and boron-delivery compounds used therein.

SUMMARY OF THE INVENTION

The present invention is directed to low toxicity boronated compounds and methods for their use in the treatment, visualization, and diagnosis of tumors. More specifically, the present invention is directed to low toxicity carborane-containing nitroporphyrin compounds and methods for their use particularly in boron neutron capture therapy (BNCT) or X-ray radiation therapy (XRT) for the treatment of tumors of the brain, head and neck, and surrounding tissue.

In particular, the present invention is directed to carborane-containing porphyrin compounds of the formula:

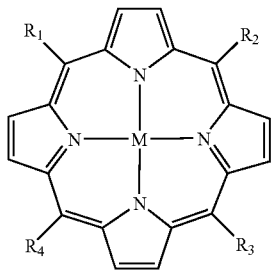

(1)

wherein:
$R^1$, $R^2$, $R^3$, and $R^4$ are independently —$NO_2$, —$NH_2$, halogen, or a substituent represented by the following formula

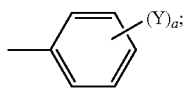

(2)

wherein Y are independently on the ortho, meta or para position on the phenyl rings, and are independently hydrogen, hydrocarbyl, non-aromatic carbocyclic, non-aromatic heterocyclic, aryl, alkylaryl, arylalkyl; or
a hydrocarbyl, non-aromatic carbocyclic, non-aromatic heterocyclic, aryl, alkylaryl, or a arylalkyl group substituted with 1 to 4 hydrophilic groups selected from hydroxy, alkoxy, —$C(O)OR^5$, —$SOR^6$, —$SO_2R^6$, nitro, amido, ureido, carbamato, —$SR^7$, —$NR^8R^9$, or poly-alkyleneoxide; or a substituent represented by formula (3)

$$—X—(CR^{10}R^{11})_r—Z \quad (3);$$

provided that at least one of $R^1$, $R^2$, $R^3$, and $R^4$ is the substituent represented by formula (2) wherein Y represents formula (3);
wherein:
X is oxygen or sulfur;
$R^5$, $R^6$, $R^7$, $R^8$, $R^9$, $R^{10}$, and $R^{11}$ are independently selected from hydrogen and $C_1$ to $C_4$ hydrocarbyl;
Z is a carborane cluster comprising at least two carbon atoms and at least three boron atoms, or at least one carbon atom and at least five boron atoms, within a cage structure;
r is 0 or an integer from 1 to 20;
a represents an integer from 1 to 4; and
provided also that at least one of $R^1$, $R^2$, $R^3$, and $R^4$ is the substituent represented by —$NO_2$, —$NH_2$, or halogen; and
M is either two hydrogen ions, a single monovalent metal ion, two monovalent metal ions, a divalent metal ion, a trivalent metal ion, a tetravalent metal ion, a pentavalent metal ion, a hexavalent metal ion, wherein the porphyrin metal complex derived from a single monovalent metal ion is charge-balanced by a counter cation, and the porphyrin-metal complex derived from a trivalent, tetravalent, pentavalent, hexavalent metal ion is charge-balanced by an appropriate number of counter anions, dianions, or trianions.

Z is preferably selected from the carboranes —$C_2HB_9H_{10}$ or —$C_2HB_{10}H_{10}$, wherein —$C_2HB_9H_{10}$ is nido ortho-, meta-, or para-carborane, and —$C_2HB_{10}H_{10}$ is closo ortho-, meta-, or para-carborane.

M is preferably vanadium (V), manganese (Mn), iron (Fe), ruthenium (Ru), technetium (Tc), chromium (Cr), platinum (Pt), cobalt (Co), nickel (Ni), copper (Cu), zinc (Zn), germanium (Ge), indium (In), tin (Sn), yttrium (Y), gold (Au), barium (Ba), tungsten (W), or gadolinium (Gd). In a more preferred embodiment, M is copper (Cu) or nickel (Ni).

In one embodiment, two of $R^1$, $R^2$, $R^3$, and $R^4$ are substituents represented by formula (2); a is 1; Y is represented by —X—$(CR^{10}R^{11})_r$—Z; $R^{10}$ and $R^{11}$ are H; r is 1; Z is —$C_2HB_{10}H_{10}$; the —X—$(CR^{10}R^{11})_r$—Z substituents are in the meta positions of the phenyl rings;
the two $R^1$–$R^4$ not represented by formula (2) are —$NO_2$ or —Br; and the substituents represented by formula (2) are in the cis conformation on the porphyrin ring.

In another embodiment, two of $R^1$, $R^2$, $R^3$, and $R^4$ are substituents represented by formula (2); a is 1; Y is represented by —X—$(CR^{10}R^{11})_r$—Z; $R^{10}$ and $R^{11}$ are H; r is 1; Z is —$C_2HB_{10}H_{10}$; the —X—$(CR^{10}R^{11})_r$—Z substituents are in the meta positions of the phenyl rings;
the two $R^1$–$R^4$ not represented by formula (2) are —$NO_2$ or —Br; and the substituents represented by formula (2) are in the trans conformation on the porphyrin ring.

In yet another embodiment, when the porphyrin compound requires a counter dianion, the counter dianion is a porphyrin compound containing a divalent negative charge. The porphyrin compound containing a divalent negative charge may be a carborane-containing porphyrin compound of the present invention, with the proviso that M is absent.

The present invention also includes methods of tumor imaging by SPECT, PET, or MRI, as well as methods of bimodal cancer treatment such as BNCT, XRT, and PDT that require the administration to a subject of a composition that comprises one or more of the porphyrin compounds described above. In a preferred embodiment, the composition is essentially one or more of the porphyrin compounds described above.

DETAILED DESCRIPTION OF THE INVENTION

The invention relates to carborane-containing nitroporphyrin compounds having the formula

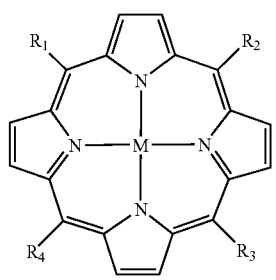

(1)

$R^1$, $R^2$, $R^3$, and $R^4$ are independently —$NO_2$, —$NH_2$, halogen, or a substituent represented by the following formula

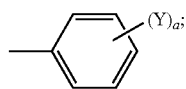

(2)

provided that at least one of $R^1$, $R^2$, $R^3$, and $R^4$ is a substituent represented by formula (2) and provided also that at least one of $R^1$, $R^2$, $R^3$, and $R^4$ is the substituent represented by —$NO_2$, —$NH_2$, or halogen Y are independently on either or both of the ortho and/or meta positions or on the para position on the phenyl rings and a represents an integer from 1 to 4. Y are hydrogen, hydrocarbyl, non-aromatic carbocyclic, non-aromatic heterocyclic, aryl, alkylaryl, arylalkyl, or a hydrocarbyl, non-aromatic carbocyclic, non-aromatic heterocyclic, aryl, alkylaryl, or arylalkyl group substituted with 1 to 4 hydrophilic groups selected from hydroxy, alkoxy, —$C(O)OR^5$, —$SOR^6$, —$SO_2R^6$, nitro, amido, ureido, carbamato, —$SR^7$, —$NR^8R^9$, or poly-alkyleneoxide, or a substituent represented by formula (3)

provided that at least one of Y is a substituent represented by formula (3).

In formula (3), X is oxygen or sulfur, $R^5$, $R^6$, $R^7$, $R^8$, $R^9$, $R^{10}$, and $R^{11}$ are independently selected from hydrogen and $C_1$ to $C_4$ hydrocarbyl, and r is 0 or an integer from 1 to 20.

Z is a carborane cluster. A carborane cluster is composed of boron and carbon atoms. Carboranes are polyhedra.

Z comprises at least two carbon atoms and at least three boron atoms, or at least one carbon atom and at least five boron atoms, within a cage structure. Some examples of carborane clusters include the regular polyhedral carborane clusters, also known as closo structures, as well as ionized fragments of the polyhedral clusters, also known as nido structures. Some examples of the preferred carboranes of the present invention include —$C_2HB_9H_{10}$ or —$C_2HB_{10}H_{10}$, wherein —$C_2HB_9H_{10}$ is nido ortho-, meta-, or para-carborane, and —$C_2HB_{10}H_{10}$ is closo ortho-, meta-, or para-carborane.

The addition of an electron-withdrawing group such as a nitro group or halogen directly attached at the meso positions on the porphyrin ring would increase the electron affinity of the porphyrin macrocycle and therefore render the resulting compound a more effective X-ray radiation sensitizer.

The electron-withdrawing groups can be —$NO_2$, —$NH_2$, or halogen. The halogen can be chlorine, fluorine, bromine, or iodine. The halogen is preferably bromine.

In a preferred embodiment, two of $R^1$, $R^2$, $R^3$, and $R^4$ are —$NO_2$. In another preferred embodiment, two of $R^1$, $R^2$, $R^3$, and $R^4$ are —Br.

Hydrocarbyl is straight chain or branched hydrocarbyl group containing 1 to 20 carbon atoms including, optionally, up to three double bond or triple bonds. Some examples of hydrocarbyl groups include methyl, ethyl, n-propyl, iso-propyl, n-butyl, iso-butyl, sec-butyl, tert-butyl, propenyl, 2-butenyl, 3-butenyl, 3-butynyl, 2-methyl-2-butenyl, n-pentyl, dodecyl, hexadecyl, octadecyl, and eicosyl.

The hydrocarbyl group may be unsubstituted or substituted with as many hydrophilic groups that the hydrocarbyl group can tolerate, e.g. 1 to 4. Some examples of suitable hydrophilic groups include hydroxy, alkoxy, —$C(O)OR^5$, —$SOR^6$, —$SO_2R^6$, nitro, amido, ureido, carbamato, —$SR^7$, —$NR^8R^9$, and poly-alkyleneoxide. $R^5$, $R^6$, $R^7$, $R^8$, and $R^9$ are independently selected from hydrogen and hydrocarbyl groups as defined above, except that the hydrocarbyl groups for $R^5$, $R^6$, $R^7$, and $R^8$ contain 1 to 4 carbon atoms.

The carbon atoms of the hydrocarbyl group may also be substituted with 1 to 4 heteroatoms. In this specification, heteroatoms are O, S, N, or $NR^{10}$. $R^{10}$ is selected from hydrogen and hydrocarbyl groups as defined above. The heteroatoms are generally not adjacent, and are preferably separated from each other by at least one carbon atom. Preferably, there is no more than one heteroatom for each two carbon atoms.

The non-aromatic carbocyclic or heterocyclic ring is a 4-, 5-, 6-, 7-, or 8-membered carbocyclic or heterocyclic ring. The ring may be saturated, or may contain as many unsaturated (i.e., double or triple) bonds as a carbocyclic ring can tolerate.

Some examples of saturated carbocyclic rings include cyclobutane, cyclopentane, cyclohexane, and cyclopentane rings. Some examples of unsaturated carbocyclic rings include cyclobutene, cyclopentene, cyclohexene, and 1,3-cycloheptadiene rings.

The heterocyclic ring comprises as many heteroatoms, i.e. O, S, N, or $NR^{10}$, as the heteroatom can tolerate, e.g. 1 to 4. Some examples of saturated and unsaturated non-aromatic heterocyclic rings include pyrrolidinyl, piperidine, piperazine, tetrahydrofuran, furan, thiophene, 1,3-oxazolidine, imidazole, and pyrrole rings. The heterocyclic rings may be optionally substituted with hydrocarbyl as defined above, or with 1 to 4 hydrophilic groups, also as defined above.

The non-aromatic carbocyclic or heterocyclic ring may be a bicyclic ring. Some examples of carbocyclic rings are bicyclco[2.2.2.]octane, bicyclo[3.1.1.]heptane, bicyclo[3.3.0.]octane, and bicyclo[4.3.0.]non-3-ene. Examples of non-aromatic heterocyclic rings include 1,4 azabicyclo[2.2.2.]octane and 2-azabicyclo[3.1.1.]heptane.

An aryl group can be either aromatic carbocyclic or heterocyclic group. An aromatic carbocyclic ring is preferably phenyl.

The aryl rings may be optionally substituted with hydrocarbyl as defined above to produce alkylaryl or arylalkyl groups. The aryl, alkylaryl, and arylalkyl groups may be substituted with 1 to 4 hydrophilic groups, as defined above.

Aromatic heterocyclic rings comprise 1 to 4 heteroatoms, i.e. O, S, N, or $NR^{10}$. The rings are typically 5-, 6-, or 7-membered. Some examples of aromatic heterocyclic rings include thiophene, pyridine, oxazole, thiazole, oxazine, and pyrazine rings. The aromatic heterocyclic ring may be substituted with 1 to 4 hydrophilic groups, as defined above.

Any of the above rings may also be fused to 1 to 3 additional 5-, 6-, or 7-membered aryl rings. Some examples of fused rings include napthalene, anthracene, phenanthrene, triphenylene, chrysene, indoline, quinoline, and tetraazanaphthalene (pteridine) rings.

In this specification, an alkoxy group contains a hydrocarbyl portion as defined above. Some examples of alkoxy groups include methoxy, ethoxy, propoxy, n-butoxy, t-butoxy, and dodecyloxy.

A polyalkylene oxide is defined according to the formula —$(CH_2)_d$—O—[$(CH_2)_e$—O—]$_x$—[$(CH_2)_f$—O—]$_y$—$(CH_2)_g$—OR', wherein, independently, d is 0, or an integer from 1 to 10, e is 0, or an integer from 1 to 10, f is 1 to 10, g is 1 to 10, x and y are each independently 1 or 0, and R' is either H or a hydrocarbyl group as defined previously, provided that when e is 0, then x is 0; when f is 0, then y is 0; when e is not 0, then x is 1; and when f is not 0, then y is 1.

A preferable polyalkylene oxide of the invention is polyethylene oxide. Polyethylene oxide is defined according to the formula —$(CH_2)_d$—O—[$(CH_2)_e$—O—]$_x$—[$(CH_2)_f$—O—]$_y$—$(CH_2)_g$—OR', wherein, independently, d is 0 or 2, e is 0 or 2, f is 0 or 2, g is 2, x and y are each independently 1 or 0, and R' is either H or an ethyl group, provided that when e is 0, then x is 0; when f is 0, then y is 0; when e is not 0, then x is 1; and when f is not 0, then y is 1.

In formula (1), M may be two hydrogen ions, a single monovalent metal ion, or two monovalent metal ions. Some examples of suitable monovalent metal ions include $Li^{+1}$, $Na^{+1}$, $K^{+1}$, $Cu^{+1}$, $Ag^{+1}$, $Au^{+1}$, and $Tl^{+1}$. When M is a single monovalent metal ion, the resulting porphyrin-metal complex anion is charge-balanced by a counter cation. Some examples of counter cations include any of the foregoing monovalent-metal ions, and ammonium and phosphonium cations, such as tetramethylammonium, tetrabutylammonium, tetraphenylaammonium, tetramethylphosphonium, tetrabutylphosphonium, and tetraphenylphosphonium. The counter cation may be either bound or associated in some form with the porphyrin-metal complex.

M may also be a divalent metal ion. Some examples of suitable divalent metal ions include $V^{+2}$, $Mn^{+2}$, $Fe^{+2}$, $Ru^{+2}$, $Co^{+2}$, $Ni^{+2}$, $Cu^{+2}$, $Pd^{+2}$, $Pt^{+2}$, $Zn^{+2}$, $Ca^{+2}$, $Mg^{+2}$, $Sr^{+2}$, and $Ba^{+2}$.

Alternatively, M may be a trivalent, tetravalent, pentavalent, or hexavalent metal ion. Some examples of suitable trivalent metal ions include $Gd^{+3}$, $Y^{+3}$, $In^{+3}$, $Cr^{+3}$, $Ga^{+3}$, $Al^{+3}$, $Eu^{+3}$, and $Dy^{+3}$. Some examples of suitable tetravalent metal ions include $Tc^{+4}$, $Ge^{+4}$, $Sn^{+4}$, and $Pt^{+4}$. An example of a suitable pentavalent metal ion is $Tc^{+5}$. Some examples of suitable hexavalent metal ions include $W^{+6}$, $Tc^{+6}$, and $Mo^{+6}$.

The resulting porphyrin-metal complex cation is charge-balanced by an appropriate number of counter anions. The anions may be monoanions, dianions, or trianions. For example, a porphyrin-metal complex cation derived from a trivalent metal ion may be charge-balanced by a single counter monoanion, and such a complex derived from a tetravalent metal ion may, for example, be charge-balanced by a single counter dianion or two counter monoanions, and so on.

Some examples of suitable counter monoanions include chloride, perchlorate, sulfate, nitrate, and tetrafluoroborate. Some examples of suitable counter dianions include oxide, sulfide, or a porphyrin compound containing a divalent negative charge. The porphyrin compound containing a divalent negative charge may be a porphyrin compound of the present invention with the proviso that M is absent. An example of a suitable counter trianion includes phosphate.

The counter monoanion, dianion, or trianion may be either bound or associated in some form with a carborane-containing porphyrin compound of the present invention. The carborane-containing porphyrin compound may also be bound to or associated with neutrally charged molecules, such as molecules of solvation, for example, water, acetonitrile, methanol, and so on.

M may be a radioactive metal ion imageable by single photon emission computed tomography (SPECT) or positron emission tomography (PET). Some examples of radioactive metals suitable for SPECT are $^{67}Cu$, $^{99m}Tc$, $^{111}In$, and those for PET include $^{64}Cu$, $^{55}Co$. M may also be a radioactive metal useful as a radiopharmaceutical for therapy. Some examples of radioactive metals suitable for such therapy include $^{90}Y$, $^{188}Re$, $^{67}Cu$.

M may also be a paramagnetic metal ion detectable by magnetic resonance imaging (MRI). Some examples of such metals include Mn, Fe, Co, and Gd.

In addition, M may be a metal ion suitable for boron neutron capture therapy (BNCT), X-ray radiation therapy (XRT), or photodynamic therapy (PDT); or a combination thereof. The metal ions suitable for BNCT include those described thus far, with the exclusion of those that are photoactive, such as Zn and Sn. Such photoactive metals, and particularly those with long-lived triplet states, are preferable for PDT. Since the dosage for BNCT is 100 to 1000 times greater than the dosage for PDT, a significant accumulation of photoactive metal in the skin could result if such photoactive metals were used in BNCT. Such an accumulation of photoactive metal may cause biological damage. For these reasons, photoactive metals such as Zn and Sn are not desirable for BNCT or XRT since even low accumulations in skin can cause skin damage. Non-photoactive metals such as Cu, Co, or Ni would be preferable. Moreover, for XRT, high Z ions such as Pt or Au, may even provide additional cell killing effects if the X-ray energies are above their K edge.

The invention also relates to methods of treating tumors. In a preferred embodiment, the method of treating malignant tumors, especially brain tumors, is BNCT. Clinical BNCT for malignant brain tumors was carried out at the Brookhaven National Laboratory Medical Department using p-boronophenylalanine (BPA) as the boron carrier (Chanana et al., Neurosurgery, 44, 1182-1192, 1999).

The description of BNCT from the Chanana et al. article is incorporated herein by reference. Those having ordinary skill in the art can readily adapt the method to the compounds of the invention.

In BNCT of malignant brain tumors following the method of the present invention, for example, the patient is first given an infusion of a carborane-containing porphyrin of formula (1), which is highly enriched in boron-10. The carborane-containing porphyrin is then concentrated preferentially in the brain tumor within the effective irradiation volume, which, for brain tumors may be a substantial part of the brain. For example, tumors located in most or all of one hemisphere and some or all of the contralateral hemisphere of the brain can accumulate boronated porphyrins.

The tumor area is then irradiated with thermalized neutrons (primary irradiation), some of which are captured by the boron-10 concentrated in the tumor. The relative probability that the slow-moving thermal neutrons will be captured by the boron-10 nuclide is high compared to the probability of capture by all of the other nuclides normally present in mammalian tissues, provided that boron-10 concentrations in tumor tissues is greater than 30 µg/g.

Since a minuscule proportion of the boron-10 nuclei in and around a tumor undergoes the nuclear reaction immediately after capturing a neutron, a high concentration of boron-10 in the targeted tissue is necessary for BNCT to be clinically effective. Therefore, to maximize the concentration of boron-10 in the targeted tissue, the carborane clusters are highly enriched in boron-10. Specifically, the boron in the carborane cluster is enriched to at least 95 atom % in boron-10.

An advantage of the present invention over the prior art for the treatment of cancer is that the boron-containing porphyrins of the present invention selectively accumulate in neoplasms in higher concentration and with higher tumor to normal brain and blood boron ratios than the currently clinically used boron-containing compounds.

Additionally, the porphyrin compounds of the present invention that have been tested in vivo are non-toxic at theoretically therapeutic effective doses. The higher selectivity and lower toxicity of the carborane-containing porphyrins of the present invention allow for the selective destruction of tumor tissue with minimal disruption of normal tissues and tissue function when irradiated.

Another advantage of the carborane-containing porphyrins of the present invention is their increased polarity, imparted through polar groups $NO_2$, $NH_2$, and halogen. The greater polarity of such groups render the porphyrin compounds less lipophilic, which can effect a reduction of the amount of an emulsifying co-solvent during administration. Therefore, the microlocalization within the tumor cell may be improved yielding a higher relative biological effect. HPLC results show that the dinitro porphyrins and dibromo porphyrins are more polar as they have shorter retention times than copper tetra-phenyl-carboranyl porphyrin (CuTCPH) or copper octabromo-tetra-carboranyl-phenyl porphyrin (CuTCPBr).

In addition, when X of the porphyrins is oxygen, the ether linkages in the carborane-containing porphyrins of the present invention are more polar than carbon-carbon linkages and therefore, provide a further reduction in lipophilicity. At the same time, the ether linkages possess nearly the same resistance to hydrolysis and other forms of chemical attack as a carbon-carbon linkage.

To accumulate the requisite amount of a compound of the present invention in a tumor, generally a systemically injected or infused dose of about 10-50 milligrams of boron-10 per kg body weight in a pharmaceutically acceptable carrier is administered to a patient. The carrier may include such commercially available solvents as Cremophor EL, propylene glycol, Tween 80, polyethylene glycol, or liposomes. The compound is administered in one or more doses, the last dose being given between about one hour and one week prior to the epithermal neutron irradiation.

The timing of the neutron exposure depends upon the concentration of the porphyrin in the blood, which decreases more rapidly with time than the porphyrin concentration in the tumor. However, the timing of the administration of the carborane-containing porphyrin depends on various considerations that are well known to those skilled in the art of clinical BNCT, including the pharmacokinetic behavior of the compound, (e.g., the rate of absorption of the compound into the tumor and into the tumor vasculature) and the rate of excretion, from and/or metabolism of the compound in, the tumor and various other tissues that absorb the compound.

In another preferred embodiment, the method of treating malignant tumors of the present invention is XRT. Typically, XRT is conventional radiotherapy that involves low LET X-ray radiation given in multiple fractions over a period of weeks. Additionally, it can also encompass radiosurgery, such as gamma knife, which is given in significantly fewer fractions or even a single fraction. In any case, a radiation enhancement agent can be given prior to irradiation as a bimodal treatment. Currently, such enhancement agents have comprised compounds such as nitroimidazole or Gd texaphyrin. In the present invention, the enhancement is based on the selective accumulation of the porphyrin in tumor tissue within the treatment volume, so that subsequent irradiation would selectively damage tumor tissue over normal surrounding tissues.

In another preferred embodiment, the method of treating malignant tumors of the present invention is PDT. PDT is a bimodal cancer treatment based on the selective accumulation of a porphyrin in a tumor, followed by irradiation of the tumor with laser red light. Upon activation with light, an electron of the porphyrin is excited from the singlet ground state to a singlet excited state. The electron then can either return to the singlet ground state with the emission of light causing fluorescence, or it can change its spin via intersystem crossing to the triplet state. In the decay of the triplet back down to the ground state singlet, it can transfer energy to ground state triplet dioxygen which forms the highly reactive singlet oxygen. Biomolecules that react most readily with singlet oxygen include unsaturated lipids and alpha amino-acid residues, both of which are major constituents of biological membranes. Beyond a certain reversible or repairable threshold, damage to membranes, especially to endothelial cell membranes, can lead to local vascular thrombosis and shutdown of blood circulation.

In using PDT in the present invention, the patient is first given an injection or infusion of a photosensitizing carborane-containing porphyrin of formula (1). Fiber-optic probes are then used to illuminate the tumor tissue. For malignant tumors, it is preferable that the PDT photosensitizers have optical absorbance peaks at sufficiently long wavelengths for maximum penetration to the depth of the tumor.

In a preferred embodiment, the therapeutic treatment of malignant tumors is augmented by the use of SPECT or PET. In SPECT, the patient is first given an infusion or injection of a compound of formula (1) wherein M is a gamma-emitting radioactive metal ion. The patient's head is then scanned noninvasively and the radionuclide concentration, and hence indirectly, the average boron concentration, in each pixel or voxel representing brain or brain tumor tissue is imaged. Contour lines representing zones of equal boron-10 concentration can thereby be drawn on each image of the brain.

SPECT of the brain is at least one order of magnitude more sensitive to isotopic tracers than is conventional radiography or computerized tomography. In addition, SPECT results, as opposed to results from conventional radiography, can be analyzed to provide quantitative information either in defined volumes or voxels of the brain images, in the concentrations of boron relevant to BNCT treatment planning and implementation. SPECT scanning can indicate the presence of a tumor in the patient, as well as its location in the brain or elsewhere in the body. SPECT scanning is noninvasive, fast, and convenient.

However, the positron emitting PET-imageable radioisotope Cu-64, is more readily available than is Cu-67, used in SPECT. Because of the much greater availability of Cu-64, we have carried out preclinical PET studies using a Cu-64 labeled porphyrin.

In another preferred embodiment, the therapeutic treatment of malignant tumors is augmented by the use of MRI. In MRI, a patient is first given an infusion or injection of a solution containing a carborane-containing porphyrin of formula (1) chelated to a suitable paramagnetic metal ion. For a brain tumor, the patient's head is then scanned and the paramagnetic metal ion concentration, and thus, boron concentration in the brain is imaged and quantified. MRI utilizing the compounds of the present invention may permit rapid enhanced targeting and treatment planning for neutron irradiation in BNCT before, during and after infusion when the boronated compound is being redistributed in blood, tumor, and healthy tissue.

The carborane-containing porphyrins of the present invention are synthesized through a series of separate steps. Provided below is first, a summary of the synthetic steps required for the preparation of the preferred carborane-containing nitroporphyrins of the present invention, wherein two of $R^1$, $R^2$, $R^3$, and $R^4$ are carboranylmethoxyphenyl groups and two are nitro groups. Those skilled in the art will readily be able to ascertain such reaction conditions.

The specific examples describe a preferred method for synthesizing the compounds of the present invention. The scope of this invention is not to be in any way limited by the examples set forth herein. For example, carboranylporphyrinamines and carboranylporphyrinhalides can be synthesized by using a mixture of different starting materials and proceeding with a similar synthetic reaction such as the Lindsey cyclization as shown in reaction scheme 2.

Reaction Scheme 1

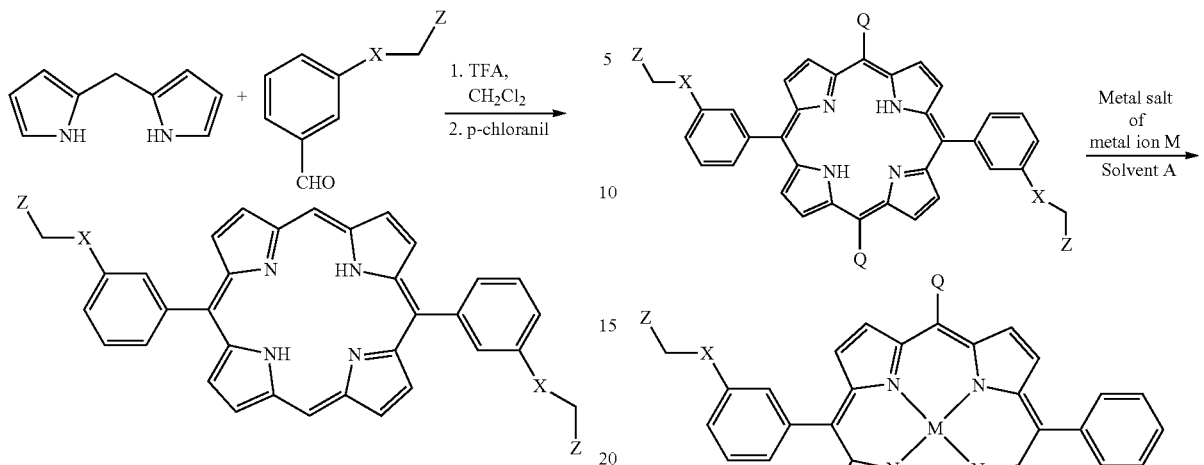

where X is either O or S and Z represents any carborane cluster comprising at least two carbon atoms and at least three boron atoms, or at least one carbon atom and at least five boron atoms, within a cage structure. Using Lindsey cyclization conditions, a Lewis acid such as boron trifluoride or a Bronsted acid such as trifluoroacetic acid is used as an acid catalyst in a nonpolar aprotic solvent such as dichloromethane (DCM). For example, the carborane cluster may be —$C_2HB_9H_{10}$ or —$C_2HB_{10}H_{10}$, wherein —$C_2HB_9H_{10}$ is nido ortho-, meta-, or para-carborane, and —$C_2HB_{10}H_{10}$ is closo ortho-, meta-, or para-carborane.

Reaction Scheme 2

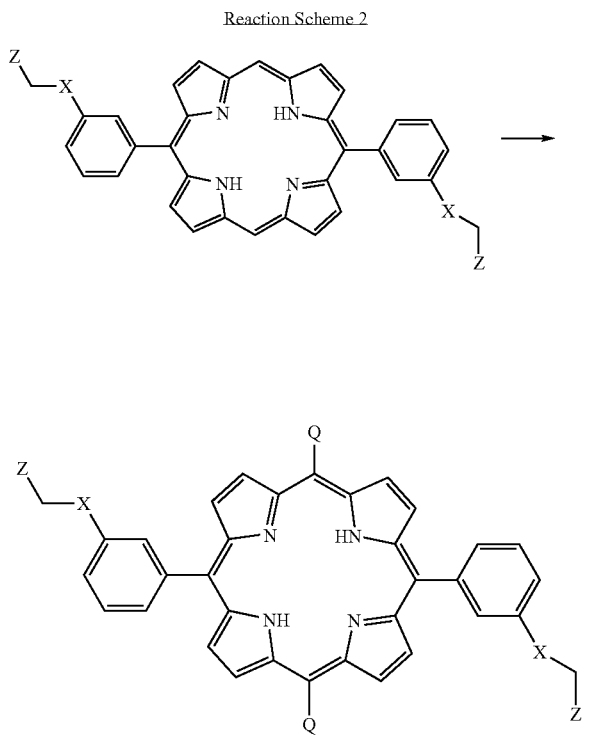

where X and Z are as previously defined. Q is —$NO_2$, —$NH_2$, or a halogen. See examples 4 and 6 below for reaction details.

Reaction Scheme 3

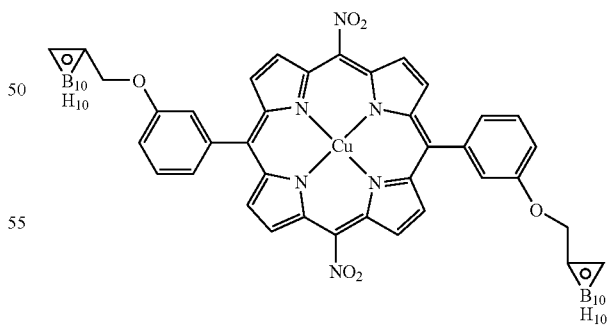

where X, Z, and Q are as previously defined. In a preferred embodiment, M is selected from the group consisting of vanadium (V), manganese (Mn), iron (Fe), ruthenium (Ru), technetium (Tc), chromium (Cr), platinum (Pt), cobalt (Co), nickel (Ni), copper (Cu), zinc (Zn), germanium (Ge), indium (In), tin (Sn), yttrium (Y), gold (Au), barium (Ba), tungsten (W), and gadolinium (Gd). In a more preferred embodiment, M is copper (Cu) or nickel (Ni). The metal salt used contains the metal ion M chelated to the porphyrin. For example, for the compound where M is desired to be copper, copper acetate, i.e., Cu(OAc)$_2$.H$_2$O, may be used as the metal salt. Solvent A is any solvent or solvent mixture capable of at least partially solubilizing the porphyrin and metal salt, and that does not interfere with incorporating the metal into the porphyrin.

Porphyrin V was prepared using reaction schemes 1-3. See examples 1-5 below for details of the synthesis. Porphyrin V has the following structure:

In Porphyrin V above, $R^1$ and $R^3$ are —$NO_2$; $R^2$ and $R^4$ are represented by formula (2); Y is represented by formula (3); $R^{10}$ and $R^{11}$ are H; r is 1; Z is —$C_2HB_{10}H_{10}$ carborane; Y are on the meta position of the phenyl rings; and M is Cu.

Porphyrin VII was prepared using reaction schemes 1-3. See examples 1-4 and 6-7 below for details of the synthesis. Porphyrin VII has the following structure:

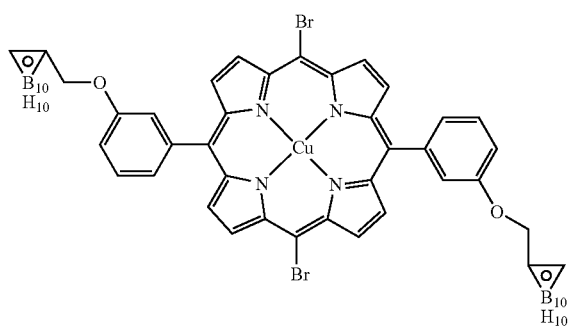

In Porphyrin VII above, $R^1$ and $R^3$ are —Br; $R^2$ and $R^4$ are represented by formula (2); Y is represented by formula (3); $R^{10}$ and $R^{11}$ are H; r is 1; Z is —$C_2HB_{10}H_{10}$ carborane; Y are on the meta position of the phenyl rings; and M is Cu.

EXAMPLES

Examples have been set forth below for the purpose of illustration and to describe the best mode of the invention at the present time. The scope of the invention is not to be in any way limited by the examples set forth herein.

Example 1

Synthesis of Pyrromethane (I)

Pyrromethane I was prepared according to the procedures in Clezy and Smythe, *Aust J Chem*, 1969, 22, 239 and Bruckner et al, *J Porph Phthal*, 1998, 2, 455. Briefly, a dipyrrylthione, which was synthesized from pyrrole and thiophosgene, was reduced with sodium borohydride to yield pyrromethane (I).

Example 2

Synthesis of 3-o-Carboranylmethoxybenzaldehyde (II)

3-o-Carboranylmethoxybenzaldehyde (II) was synthesized using the method described in Miura et al, *Tet Let*, 1990, 31, 2247-2250.

Example 3

Synthesis of Dicarboranylphenylporphyrin (III)

A procedure similar to that described by Bruckner et al, *J Porph Phthal*, 1998, 2, 455 was followed. Pyrromethane (I) (97 mg, 0.66 mmol) was dissolved in anhydrous DCM (120 mL) in a clean dry 250 mL flask equipped with a magnetic stir bar. The solution was deoxygenated by bubbling nitrogen into the stirring solution for 10 min. 3-o-Carboranylmethoxybenzaldehyde (II) (172 mg, 0.699 mmol) was added and the solution was deoxygenated for another 5 min. Trifluoroacetic acid [TFA] (11.5 mL, 0.155 mmol) was added and the solution was allowed to stir under a nitrogen atmosphere at room temperature overnight. After ~18 hours, p-chloranil (500 mg, 2.03 mmol) was added, after which the solution immediately turned to a dark burgundy color. The solution was allowed to reflux for 1 hour when the optical absorption spectrum showed the desired porphyrin. Aqueous sodium bisulfite was added to reduce excess p-chloranil to the hydroquinone for easier purification. After 10 min, the reaction was worked up by dilution with DCM, washing the organic layer with water/brine a few times and drying the organic layer with anhydrous sodium sulfate. The solvents were removed and the red residue was triturated with methanol to remove the hydroquinone. The purple solid was purified by flash chromatography (silica, 30% hexane/DCM) yielding ~27 mg (~9% yield).

The product gave the following proton nuclear magnetic resonance ($^1$H NMR) spectrum in ppm (in $CDCl_3$ solvent): 10.344 (s, 2H, methine H); 9.419 (d (J=4.6 Hz), 4H, pyrrole H); 9.058, (d (J=4.6 Hz), 4H, pyrrole H); 7.973 (d (J=7.1 Hz), 2H, ArH); 7.720-7.768 (m, 6H, ArH); 4.656 (s, 4H, $OCH_2$-carborane); 4.220 (s, 2H, carborane CH); 1.5-2.9 (br in, 20H, BH) −3.177 (s, 2H, NH). The ultraviolet-visible absorbance spectrum of the product (in dichloromethane solvent) showed the following peaks in nanometers of wavelength: 406, 502, 535, 574.

Example 4

Synthesis of 5,15-Dinitro-10,20-bis(3-[o-carboranylmethoxy]phenyl)porphyrin (IV)

A procedure similar to that described in Arnold et al, *Aus J Chem*, 1997, 50, 495-503 was followed. Dicarboranylphenylporphyrin (III) (20 mg, 0.025 mmol) was dissolved in anhydrous 1,2-dichloroethane (DCE) (15 mL) and anhydrous acetonitrile (15 mL) in a clean, dry 100 mL flask equipped with a stir bar under a nitrogen atomosphere. Iodine (64 mg, 0.25 mmol) dissolved acetonitrile (5 mL) was added to the porphyrin solution, which was then allowed to stir at reflux for 1 hour. At this time silver nitrite (80 mg, 0.53 mmol) in acetonitrile (5 mL) was added to the porphyrin solution, which was allowed to stir at reflux for another 2 hours and then room temperature overnight. TLC (silica, 30% hexane/DCM) showed a new product at almost the same Rf, but was green instead of red. The optical spectrum showed what appeared to be desired product. The reaction mixture was filtered through sintered glass and the solvents removed in vacuo. The residue was dissolved in chloroform and eluted through a short silica pad.

The product gave the following proton nuclear magnetic resonance ($^1$H NMR) spectrum in ppm (in $CDCl_3$ solvent): 9.31 (d (J=4.1 Hz) 4H, pyrrole H); 9.00 (d (J=4.1 Hz), 4H, pyrrole H); 7.889 (m, 2H, ArH); 7.739-7.778 (m, 2H, ArH); 7.65-7.671 (m, 2H, ArH); 7.339-7.365 (m, 2H, ArH); 4.650 (s, 4H, $OCH_2$-carborane); 3.490 (s, 2H, carborane CH); 1.5-2.9 (br m, 20H, BH); −3.10 (s, 2H, NH). The ultraviolet-visible absorbance spectrum of the product (in dichloromethane solvent) showed the following peaks in nanometers of wavelength: 421, 513, 555, 589, 652.

Example 5

Synthesis of Copper (II) 5,15-dinitro-10,20-bis(3-[o-carboranylmethoxy]phenyl)porphyrin (V)

Free base 5,15-dinitro-10,20-bis(3-[o-carboranylmethoxy]phenyl)porphyrin (IV) was dissolved in chloroform and to it was added copper (II) acetate monohydrate. The mixture was allowed to stir at reflux overnight. Optical spectroscopy showed metallation was complete. Reaction was worked up by diluting with DCM and washing three times with water, drying (anhydrous sodium sulfate) and removal of solvents.

The ultraviolet-visible absorbance spectrum of the product (in dichloromethane solvent) showed the following peaks in nanometers of wavelength: 426, 545, 583.

Example 6

Synthesis of 5,15-dibromo-10,20-bis(3-[o-carboranylmethoxy]phenyl)porphyrin (VI)

The dicarboranylporphyrin III was treated with N-Bromosuccinimide (NBS) in a procedure similar to that described by C. Liu et al. (Chem Comm 2006, 770-772) whereby the starting porphyrin IV (126 mg, 0.156 mmol) was dissolved in a DCM:methanol mixture (9/1 v/v; 30 mL). To this stirring solution at room temperature, NBS (55.6 mg, 0.312 mmol) was added. After ~15 minutes the optical absorption spectrum and TLC (in 50% hexane in DCM) showed no starting material. The optical spectrum showed the Soret band had red-shifted from 406 to 421 nm and the TLC showed a less polar product. The reaction was quenched by the addition of water and the reaction was worked up. The crude product was purified using a pad of silica eluting with DCM. Further purification was done by filtering off product (48 mg) that was not soluble in DCM and combining it with product (44 mg) that was purified by preparative TLC (silica; 10% ethyl acetate in hexane). By HPLC analyses, the filtered product was 90% pure and that from TLC was 83% pure. The combined yield for 100% purity was 84 mg (53% yield).

Proton NMR showed that the meso protons were no longer present. ($^1$H NMR) spectrum in ppm (in CDCl$_3$ solvent): 9.628 (d(J=3.6 Hz) 4H, pyrrole H); 8.815 (d (J=4.4 Hz), 4H, pyrrole H); 7.867 (d, 2H, ArH); 7.654-7.725 (m, 4H, ArH); 7.296-7.324 (m, 2H, ArH); 4.628 (s, 4H, OCH$_2$-carborane); 4.190 (s, 2H, carborane CH); 1.5-3.0 (br m, 20H, BH); −2.766 (s, 2H, NH).

Example 7

Synthesis of copper (II) 5,15-dibromo-10,20-bis(3-[o-carboranylmethoxy]phenyl)porphyrin (VII)

The dibromoporphyrin VI free base was metallated to form the Cu(II) porphyrin with copper acetate using the same procedure described in Example 5. 124 mg of copper porphyrin VII was obtained that was 90% pure by HPLC analysis. UV-Vis spectrum in DCM$_{max}$ (nm): 418, 546. C$_{38}$H$_{42}$N$_4$O$_2$B$_{20}$Br$_2$Cu requires 1026.330; MALDI-TOF in dithranol matrix: m/z=1026.93.

Example 8

Preparation of Porphyrin Solutions

Porphyrin compound (V) was emulsified in 9% Cremophor EL and 18% propylene glycol in saline.

To prepare a solution of ~3.7 mg/mL porphyrin in 9% Cremophor EL (CRM) and 18% propylene glycol (PRG), the porphyrin was dissolved in tetrahydrofuran (THF) (1.5% of the total volume) and then heated to 40° C. for 15 min. CRM (9% of total volume) was then added and the mixture was heated to 60° C. for 2 hours, which removed most of the THF. After cooling to room temperature, PRG (18% of total volume) was added, followed by slow dropwise addition of saline (71.5% of total volume) with rapid stirring. The solution was degassed by stirring under vacuum (~30 mm Hg) for 30-60 min and then filtered (Millipore, 8 μm).

Example 9

Biodistribution of Porphyrin Compound V in Mice Bearing EMT-6 Carcinomas

BALB/c mice bearing subcutaneously implanted EMT-6 mammary carcinomas implanted on the dorsal thorax were given a total dose of 105 milligrams porphyrin compound V per kilogram body weight (23.7 mg B/kg). At one and two days after the last injection, mice were euthanized, and tumor, blood, brain, and liver were removed for boron analyses. The blood was first analyzed for hematologic parameters that indicate toxicity before it was analyzed for boron. Table 1 shows the average boron concentrations for different types of tissue from BALB/c mice.

TABLE 1

Average boron concentrations (μg/g wet tissue) in various tissues in mice (n = 5) given 105 mg/kg porphyrin compound V (23.7 mg B/kg) in 3 i.p. injections over a period of 8 hours at either 1 or 2 days after the last injection. Values are reported as mean and standard deviation.

| | Time after last injection (days) | |
|---|---|---|
| | 1 | 2 |
| Number of mice | 5 | 5 |
| Tumor (μg B/g) | 39.2 ± 14.4 | 49.8 ± 12.9 |
| Blood (μg B/g) | 34.6 ± 26.9 | 1.5 ± 0.4 |
| Skin (pinna) (μg B/g) | 3.6 ± 13.0 | 4.8 ± 1.6 |
| Brain (μg B/g) | 0.5 ± 0.4 | 0.1 ± 0.1 |
| Liver (μg B/g) | 145 ± 38 | 226 ± 25 |
| Spleen (μg B/g) | 76.1 ± 8.6 | 158 ± 19 |
| Kidneys (μg B/g) | 12.7 ± 6.9 | 7.1 ± 0.5 |
| Lungs (μg B/g) | — | 8.5 ± 3.0 |
| Heart (μg B/g) | 9.1 ± 3.8 | 7.5 ± 0.6 |
| Feces (μg B/g) | — | 15.2 ± 20.8 |

Example 10

Weight Changes and Hematologic Parameters from Porphyrin V

TABLE 2

Weight changes and hematologic parameters in mice given 105 mg/kg porphyrin compound V (23.7 mg B/kg) at 1 or 2 days after the last injection. Values are reported as mean and standard deviation.

| Compound | Porphyrin compound V | Control | Porphyrin compound V | Control |
|---|---|---|---|---|
| Time after last injection (days) | 1 | 1 | 2 | 2 |
| % Weight change | −0.8 ± 1.8 | 0 ± 2.7 | −1.7 ± 1.7 | 2.1 ± 1.4 |
| Platelet count (m/m$^3$) | 1349 ± 294 | 1276 ± 83 | 515 ± 160 | 1138 ± 258 |
| White blood count (m/m$^3$) | 9.9 ± 2.6 | 4.9 ± 2.2 | 11.8 ± 1.8 | 7.5 ± 2.0 |

The results of the preliminary biodistribution study showed that porphyrin compound V appears to be a promising candidate as a sensitizer for both BNCT and XRT. Although the tumor:blood boron ratio is only 1:1 one day after the injections, it increased to >30:1 two days after the injections. From a relatively low porphyrin dose of only ~100 mg/kg (24 mg/kg B), a considerable amount of boron, ~50 ppm, was delivered to the tumor. By contrast, liver and spleen values are lower than would be expected even from this low dose. The boron and porphyrin tumor targeting capability as measured by the percentage of injected dose in tumor per gram of wet tissue (~10.5%/g) would be considered quite efficient in comparison to CuTCPH, the most studied porphyrin in this class, which has a value of 6.1 %/g in the same tumor model.

Example 11

Biodistribution of Porphyrin Compound VII in Mice Bearing EMT-6 Carcinomas

Similar to Example 8, Compound VII was given to tumor-bearing mice except at a slightly higher total dose of 143 mg/kg body weight in 3 i.p. injections given over a period of 8 hours.

TABLE 3

Average boron concentrations (μg/g wet tissue) in various tissues in mice (n = 5) given 143 mg/kg porphyrin compound VII (30 mg B/kg) in 3 i.p. injections over a period of 8 hours at either 1 or 2 days after the last injection. Values are reported as mean and standard deviation.

| | Time after last injection (days) | |
|---|---|---|
| | 1 | 2 |
| Number of mice | 5 | 5 |
| Tumor (μg B/g) | 67.1 ± 8.5 | 76.9 ± 14.1 |
| Blood (μg B/g) | 105 ± 20 | 12.1 ± 9.7 |
| Skin (pinna) (μg B/g) | 9.2 ± 1.8 | 7.7 ± 1.7 |
| Brain (μg B/g) | 1.9 ± 0.5 | 0.1 ± 0.2 |
| Liver (μg B/g) | 183 ± 19 | 263 ± 34 |
| Spleen (μg B/g) | 107 ± 11 | 160 ± 15 |
| Kidneys (μg B/g) | 38.7 ± 7.0 | 13.0 ± 3.6 |
| Lungs (μg B/g) | 35.8 ± 3.7 | 17.8 ± 6.2 |
| Heart (μg B/g) | 20.4 ± 4.6 | 9.4 ± 1.1 |
| Feces (μg B/g) | 11.2 ± 2.3 | 4.9 ± 0.6 |

Example 12

TABLE 4

Weight changes and hematologic parameters in mice given 143 mg/kg porphyrin compound VII (30 mg B/kg) at 1 or 2 days after the last injection. Values are reported as mean and standard deviation.

| Compound | Porphyrin compound VII | Control | Porphyrin compound VII | Control |
|---|---|---|---|---|
| Time after last injection (days) | 1 | 1 | 2 | 2 |
| % Weight change | −0.3 ± 1.4 | 0 ± 2.7 | 0.2 ± 2.2 | 2.1 ± 1.4 |
| Platelet count (m/m³) | 1461 ± 229 | 1276 ± 83 | 790 ± 227 | 1138 ± 258 |
| White blood count (m/m³) | 8.8 ± 1.3 | 4.9 ± 2.2 | 11.8 ± 1.8 | 11.0 ± 0.7 |

The biodistribution data from porphyrin VII in Table 3 indicate that high amounts of boron and porphyrin can be delivered to tumor tissue similar to other lipophilic porphyrins that possess four tetracarboranylphenyl moieties at the meso position instead of the two in this invention. Although the tumor:blood boron ratio was less than 1:1 at 1 day after the last injection, after one more day it increased to ~7:1 with a slightly higher tumor boron concentration. There was little if any toxicity associated with the porphyrin at this dose.

Thus, while the preferred embodiments of the present invention have been described, those skilled in the art will realize that other embodiments can be made without departing from the spirit of the invention, which include all such further modifications and changes as come within the true scope of the claims set forth herein.

The invention claimed is:
1. A method of bimodal cancer treatment in a subject comprising the administration to the subject of a composition comprising a compound of the formula

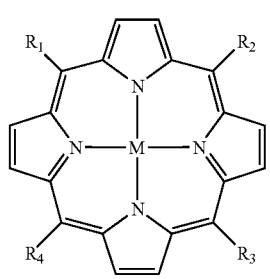

(1)

wherein:
$R^1, R^2, R^3$, and $R^4$ are independently —$NO_2$, —$NH_2$, halogen, or a substituent represented by the following formula

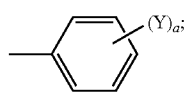

(2)

wherein Y are independently on the ortho, meta or para position on the phenyl rings, and are independently hydrogen, hydrocarbyl, non-aromatic carbocyclic, non-aromatic heterocyclic, aryl, alkylaryl, or arylalkyl; or a hydrocarbyl, non-aromatic carbocyclic, non-aromatic heterocyclic, aryl, alkylaryl, or a arylalkyl group substituted with 1 to 4 hydrophilic groups selected from hydroxy, alkoxy, —$C(O)OR^5$, —$SOR^6$, —$SO_2R^6$, nitro, amido, ureido, carbamato, —$SR^7$, —$NR^8R^9$, or polyalkyleneoxide; or a substituent represented by formula (3)

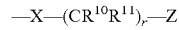

(3)

provided that at least one of $R^1$, $R^2$, $R^3$, and $R^4$ is the substituent represented by formula (2) wherein Y represents formula (3);
wherein:
X is oxygen or sulfur;
$R^5$, $R^6$, $R^7$, $R^8$, $R^9$, $R^{10}$, and $R^{11}$ are independently selected from hydrogen and $C_1$ to $C_4$ hydrocarbyl;
Z is a carborane cluster comprising at least two carbon atoms and at least three boron atoms, or at least one carbon atom and at least five boron atoms, within a cage structure;
r is 0 or an integer from 1 to 20;
a represents an integer from 1 to 4; and
provided also that at least one of $R^1$, $R^2$, $R^3$, and $R^4$ is the substituent represented by —$NO_2$, —$NH_2$, or halogen; and
M is either two hydrogen ions, a single monovalent metal ion, two monovalent metal ions, a divalent metal ion, a trivalent metal ion, a tetravalent metal ion, a pentavalent metal ion, a hexavalent metal ion, wherein the compound derived from the single monovalent metal ion is charge-balanced by a counter cation, and the compound derived from the trivalent, tetravalent, pentavalent, hexavalent metal ion is charge-balanced by an appropriate number of counter anions, dianions, or trianions; and the irradiation of said subject, wherein said irradiation comprises X-ray radiation therapy (XRT).

2. The method according to claim 1 wherein Z is selected from the carboranes —$C_2HB_9H_{10}$ or —$C_2HB_{10}H_{10}$, wherein —$C_2H_9H_{10}$ is nido ortho-, meta-, or para-carborane, and —$C_2HB_{10}H_{10}$ is closo ortho-, meta-, or para-carborane.

3. The method according to claim 1 wherein M is a metal ion suitable for X-ray radiation therapy (XRT).

4. The method according to claim 3, wherein M is vanadium, manganese, iron, ruthenium, technetium, chromium, platinum, cobalt, nickel, copper, zinc, germanium, indium, tin, yttrium, gold, barium, tungsten, or gadolinium.

5. The method according to claim 1 wherein
 i. two of $R^1$, $R^2$, $R^3$, and $R^4$ are substituents represented by formula (2);
 ii. a is 1;
 iii. Y is represented by formula (3);
 iv. Y is in the meta positions of the phenyl rings; and
 v. two of $R^1$-$R^4$ not represented by formula (2) are —$NO_2$, —$NH_2$, or halogen.

6. The method according to claim 5 wherein the substituents represented by formula (2) are in the cis configuration.

7. The method according to claim 5 wherein the substituents represented by formula (2) are in the trans configuration.

8. The method according to claim 7 wherein the two of $R^1$-$R^4$ not represented by formula (2) are —$NO_2$ or —Br.

9. The method according to claim 8 wherein Z is selected from the carboranes —$C_2HB_9H_{10}$ or —$C_2HB_{10}H_{10}$, wherein —$C_2HB_9H_{10}$ is nido ortho-, meta-, or para-carborane, and —$C_2HB_{10}H_{10}$ is closo ortho-, meta-, or para-carborane.

10. The method according to claim 9, wherein M is vanadium, manganese, iron, ruthenium, technetium, chromium, platinum, cobalt, nickel, copper, zinc, germanium, indium, tin, yttrium, gold, barium, tungsten, or gadolinium.

11. The method according to claim 10, wherein X is oxygen, $R^{10}$ and $R^{11}$ are hydrogen, and r is 1.

12. A method of bimodal cancer treatment in a subject comprising the administration to the subject of a composition comprising a compound of the formula

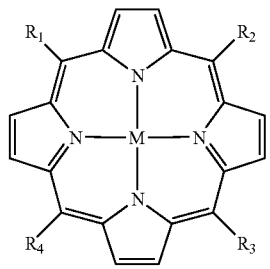

(1)

wherein:
 i. two of $R^1$, $R^2$, $R^3$, and $R^4$ are substituents represented by the following formula

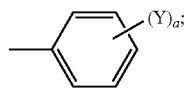

(2)

ii. a is 1;
 iii. Y is represented by the following formula

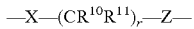

(3);

iv. Y is in the meta positions of the phenyl rings;
 v. two of $R^1$-$R^4$ not represented by formula (2) are —$NO_2$ or —Br;
 vi. the substituents represented by formula (2) are in the trans configuration;
 vii. Z is selected from the carboranes —$C_2HB_9H_{10}$ or —$C_2HB_{10}H_{10}$, wherein —$C_2HB_9H_{10}$ is nido ortho-, meta-, or para-carborane, and —$C_2HB_{10}H_{10}$ is closo ortho-, meta-, or para-carborane;
 viii. M is vanadium, manganese, iron, ruthenium, technetium, chromium, platinum, cobalt, nickel, copper, zinc, germanium, indium, tin, yttrium, gold, barium, tungsten, or gadolinium; and
 ix. X is oxygen, $R^{10}$ and $R^{11}$ are hydrogen, and r is 1;
and the irradiation of said subject, wherein said irradiation comprises X-ray radiation therapy (XRT).

* * * * *